United States Patent [19]

Dobritz

[11] 4,086,305
[45] Apr. 25, 1978

[54] HUMIDIFIER FOR RESPIRATORS HAVING A SEALED CONTAINER WATER SUPPLY TO A WATER STORAGE TANK

[75] Inventor: Günter Dobritz, Lubeck, Germany

[73] Assignee: Drägerwerk Aktiengesellschaft, Germany

[21] Appl. No.: 694,605

[22] Filed: Jun. 10, 1976

[51] Int. Cl.² .................. B01F 3/04; A61M 15/00
[52] U.S. Cl. ........................ 261/30; 128/186;
128/192; 261/36 R; 261/104; 261/130;
261/142; 261/DIG. 65
[58] Field of Search ............... 261/30, 36 R, 99, 103,
261/104, 106, 107, 142, 153, 154, DIG. 65,
129–131; 128/185–188, 191 R, 192–194, 208,
212; 210/321 A, 321 B

[56] References Cited

U.S. PATENT DOCUMENTS

| 760,673 | 5/1904 | White et al. ............... 261/106 X |
| 1,273,682 | 7/1918 | Slater et al. ............... 261/104 |
| 2,225,954 | 12/1940 | Grubb ........................ 261/103 X |
| 2,275,428 | 3/1942 | Haldeman .................. 261/36 R X |
| 2,603,468 | 7/1952 | Sutton ........................ 261/104 |
| 2,653,017 | 9/1953 | Frost .......................... 261/103 X |
| 3,616,796 | 11/1971 | Jackson ...................... 261/153 X |
| 3,871,373 | 3/1975 | Jackson ...................... 261/104 X |
| 3,912,795 | 10/1975 | Jackson ...................... 261/104 X |
| 3,916,891 | 11/1975 | Freytag et al. ............. 261/DIG. 65 |

Primary Examiner—Tim R. Miles
Assistant Examiner—Richard L. Chiesa
Attorney, Agent, or Firm—McGlew and Tuttle

[57] ABSTRACT

A humidifier for respirators includes a vessel having a tubular passage therethrough which is connected at one end to the inhalation line and the opposite end to the line leading to the patient. Water is circulated from a storage tank to a water chamber defined around the tubular member and the tubular member is made of a material which defines an evaporation surface which is impervious to water but pervious to water vapor so that the inhalation air becomes moistened when it is passed through the tubular member. The water which is circulated is circulated from a storage tank which is maintained at a predetermined level by the gravity of feed of water from a closed container which is mounted above the storage tank. The water in the storage tank is advantageously heated before it is circulated. To facilitate evaporation a continuous spiral screw is inserted into the tubular member so that the inhalation air is deflected around the tubular member between the convolutions of the screw so as to increase the moistening of the inhalation air during its passage through the vessel.

1 Claim, 2 Drawing Figures

HUMIDIFIER FOR RESPIRATORS HAVING A SEALED CONTAINER WATER SUPPLY TO A WATER STORAGE TANK

BACKGROUND OF THE INVENTION

1. Field of the Invention

This invention relates in general to the construction of humidifiers for respirators and in particular to a new and useful humidifier wherein water is circulated around an evaporation surface through which inhalation air is passed from a storage tank which is maintained at a proper level by a closed container which is supported above the level of the storage tank.

2. Description of the Prior Art

In the artificial respiration of patients by means of intubation and also in the spontaneous respiration of tracheotomiced patients, the respiratory air no longer flows through the throat-nose-pharynx tract, but directly into the bronchi. Since the respiratory air does not come into contact with the throat-nose-pharynx tract, it can no longer be heated sufficiently and humidified. The result is a drying out of the respiratory tract and an impairment of the function of the ciliary epithelium. In order to prevent the respiratory tracts from drying out, it is known to provide humidifiers whose function it is to heat the inhaling air to body temperature and if possible to bring it to a value of possibly 100% relative humidity.

The known humidifers have an essential drawback that the water which evaporates therein increases the volume of the vacuum on the inhaling side. Due to the unavoidable compression at the inhaling pressure which can amount up to 120 mm of water column a critical inhaling volume difference between respiration with and without water supply in the humidifier of about 20% may occur in the respiration of infants.

The so-called cascade humidifiers are known in which the inhaling air is conducted through the heated water which is to humidify the air. Water droplets which have been carried along are retained by pellets arranged above the water surface. A disadvantage of a cascade humidifier is that the compressible volume varies with the amount of filling water. Beyond that, the apparatus is so big that it cannot be placed directly in front of the mouth of the patient. In long feed lines, the air cools off, however a part of the moisture contained in the inhaling air will thus condense. The condensate must be kept away from the patient by corresponding measures.

Humidifiers operating with a wick operate similar to cascade humidifiers as surface humidifiers. But the air does not come in close contact with the water because of the wick. It passes by the moistened wicks which absorb heated water from a storage tank. These humidifiers have the same drawbacks as the cascade humidifiers, but since they can be built smaller they can be arranged closer to the patient. The problems of condensation are thus less pronounced but the requirement for sufficient humidification of the respiratory air is more problematic.

Another humidifier employs hot steam injection into the inhaling air current. For the production of the hot steam, a heated plate is arranged in the humidifier in which an adjustable amount of water is evaporated. The generated steam flows into the inhaling air system and humidifies and heats the system. The humidifiers according to this system can be built very small. Condensation is therefore no problem but the adjustment of the amount of water for proper humidification is difficult. A respiratory volume which is too small may result in overheating while a volume which is too great may lead to inadequate humidification and too low temperatures.

SUMMARY OF THE INVENTION

The present invention provides a respiratory humidifier in which the compressible volume remains constant independent of the water consumption and it can be built so small that it can be moved close to the patient to avoid condensation and it can be connected to enter the inhaling air feed. With the inventive arrangement water is circulated from a water storage tank through a vessel having a tubular passage bounded by an evaporation surface member through which the inhalation air is passed. The water is circulated from the storage tank around the tubular member and returned into the storage tank. The storage tank is maintained filled with liquid by a gravity feed from a water supply container which is tightly sealed and arranged above the storage tank to discharge continuously into the storage tank. It insures that water cannot penetrate under any circumstances into the respirator if the evaporation surface should become loosened. Air enters through a hole in the evaporation surface from the inhaling line into the water space, sucked in by the water column and the water feed and water discharge lines. Due to the entrance of air the water space and the two lines then run empty.

In a further development the evaporation surface is arranged as a tube extending axially through the housing and the interior of the tube contains a single or multi-threaded axially mounted screw. The screw is rotatable and the inhalation air passes between the convolutions of the screw through the tube and produces a rotation of the screw. This causes a transportation of the inhalation air along in contact with the interior of the tube by the revolving screw so that an excellent moisture transfer can take place. A special energy source for rotating the screw is not necessary because at the low velocity of flow of pressure drop in the inhaling line is negligible.

Accordingly it is an object of the invention to provide an improved humidifier which includes a tubular member defining an evaporation surface in a vessel between an inlet and an outlet and which is located within a water chamber which is fed with water from a storage tank and which includes a water receiver tank which is tightly sealed and has a discharge line which feeds by gravity into the storage tank.

A further object of the invention is to provide a humidifier which includes a vessel having a tubular passage extending between an inlet and an outlet of the vessel and a surrounding water chamber through which water is circulated and wherein the tubular passage includes a screw which is rotatable and between the convolutions of which the inhalation air is passed, the evaporation surface permitted transfer of water vapor into the air stream.

A further object of the invention is to provide a humidifier which is simple in design, rugged in construction and economical to manufacture.

For an understanding of the principles of the invention, reference is made to the following description of typical embodiments thereof as illustrated in the accompanying drawing.

GENERAL DESCRIPTION OF THE PREFERRED EMBODIMENTS

Figure 1:
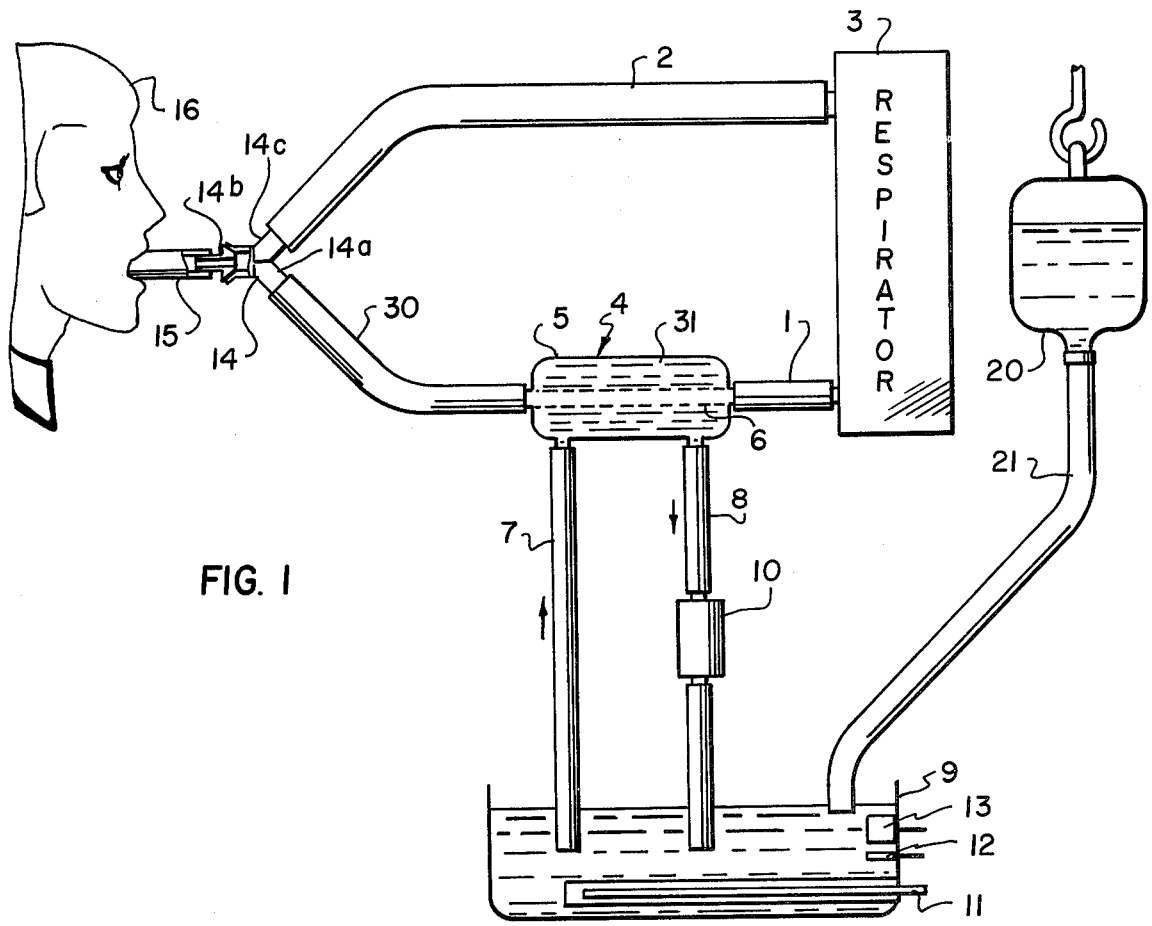
FIG. 1 is a schematic partial elevational and partial sectional view of a respiratory humidifier constructed in accordance with the invention.

Referring to the drawings in particular the invention embodied therein in FIG. 1 comprises a respiratory air humidifier which includes an inhaling line leading from the respirator 3 which connects to an inlet end of a humidifier generally designated 4 which has an interior passage defined by a tubular evaporation surface 6 with a discharge leading through a discharge line 30 to one leg 14a of a Y-shaped mouthpiece 14. A central portion 14b of the mouthpiece connects through a tubular extension 15 to a patient 16. The other leg 14c of the mouthpiece is connected to the exhaling air line 2 which returns to the respirator 3.

In accordance with the invention the evaporator surface 6 comprises a tube made of a material which is pervious to water vapor but impervious to water. Water is contained in an annular chamber 31 of a vessel 5 of the humidifier 4 during the operation by circulation of water from a storage tank 9 upwardly through a water feed line 7. The water is returned through a return line 8 to the storage tank 9 and circulation is effected by a pump 10.

In the storage tank 9 the water is brought to a predetermined temperature by means of a heater 11 which is controlled by a thermostat 12 to preferably heat the water to 36° C. In accordance with a feature of the invention a water supply is maintained in a tightly sealed receiver or container 20 and the water is delivered through a discharge line 21 by gravity into the storage tank 9 to replenish it to a predetermined level. The water will flow into the tank 9 even if the water level of the storage tank 9 drops below the inlet end of the discharge line 21. A dry-out protection device 13 includes means such as a alarm warning when the water supply drops too low or a control which effects a feeding of water into the tank on such occasions.

Water is picked up by the inhalation air flowing into the inlet of the vessel from the inhalation line 1 due to the movement of the water vapor through the evaporation surface 6. The water vapor becomes entrained in the inhaling air current which then flows through the leg 14a of the mouthpiece 14 to a mouthpiece tube 15 and the patient 16. The unevaporated water flows in a cycle back to the storage tank 9 through the return line 8. The circuit arrangement insures that the respiratory humidifier 4 is always traversed by water of the desired temperature. The respiratory humidifier 4 is arranged directly in front of the Y-piece 14 and thus it may be positioned close to the patient 16 so that cooling of the air caused by condensation on connecting lines will be prevented.

The storage tank 9 is arranged under the vessel 5 and the water feed line 7 and the water return line 8 depend from the vessel into the storage tank. The supply and return lines 7 and 8 protrude below the water surface in the storage tank 9.

The arrangement of the receiver 20 above the storage tank 9 insures that the spent water can flow in automatically up to a given level. If the evaporation surface 6 should be insufficiently tight air would enter from the inhaling line 1 into the water space 31, sucked in by the water columns in the water feed line 7 and the water discharge line 8. Due to the entrance of such air the water space and the two lines run empty. It is impossible that water can get into the inhaling line 1 therefore when the surface 6 does become unfastened for one reason or the other.

Figure 2:
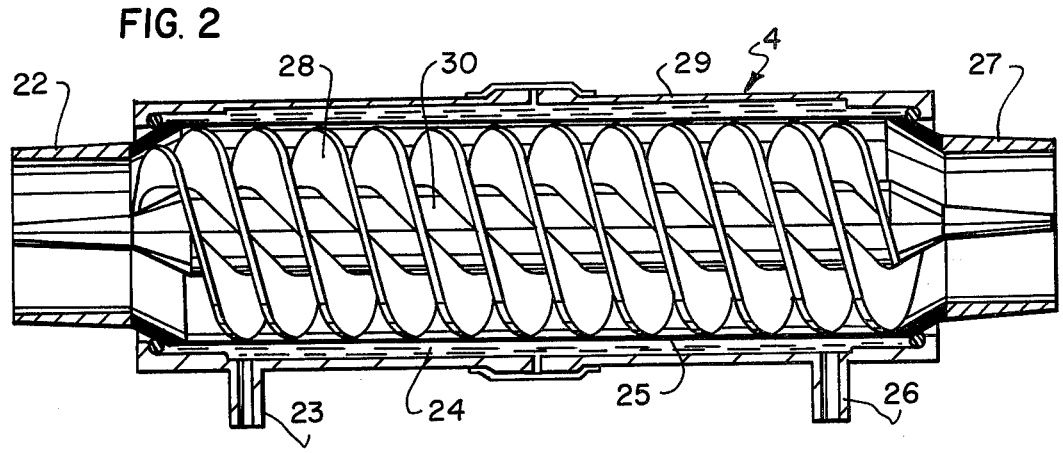
FIG. 2 is an enlarged partial sectional view of another embodiment of the humidifier.

In the embodiment shown in FIG. 2 a humidifier generally designated 4 includes a housing 29 of tubular construction having a water space 24 which is sealed to the interior wall by an evaporation surface designed as a tube 25 which extends between the inlet and outlet to the housing 29. The water feed line is connected to a water infeed connection 23 and a water return line or discharge line is connected to a return connection 26. An inhaling line connection or fitting 27 connects to an inhaling line and a discharge line 22 connects to the Y-piece used by the patient. In accordance with a feature of this embodiment the inner cavity 30 contains a single or multi-threaded axially mounted screw 28 which is rotatable within the evaporation surface tube 25. The screw is set in rotation by the movement of the air during inhalation. The inhalation air is thus deflected to the moist tube between the convolutions of the screw and the close contact path of travel which the air takes results in a maximum evaporation of the water.

While specific embodiments of the invention have been shown and described in detail to illustrate the application of the principles of the invention, it will be understood that the invention may be embodied otherwise without departing from such principles.

What is claimed is:

1. A humidifier for use with respirators, comprising a vessel having an inlet end connectable to an inhaling line and an outlet end spaced from said inlet end connectable to the user, means defining a passage between said inlet and said outlet having at least a portion with a wall defining an evaporation surface pervious to water vapor but impervious to water, means defining a water chamber in said vssel in contact with said evaporation surface, a water storage tank below said vessel, an inlet line and a return line for water depending from said vessel and extending downwardly from said water chamber into said water storage tank, means for circulating water from said storage tank to said water chamber through said inlet line and into said water chamber and to said return line, a separate replaceable sealed water container located above said storage tank, for supplying water to said storage tank and a discharge conduit connected between said sealed water container and said water storage tank, an axially progressing screw rotatable in said passage and adjacent said evaporation surface and being rotatable by the flow of inhalation air between the convolutions thereof to direct the air outwardly into intimate contact with the surface.

* * * * *